US00PP08412P

United States Patent [19]

Saville

[11] Patent Number: Plant 8,412

[45] Date of Patent: Oct. 12, 1993

[54] MINIATURE ROSE PLANT NAMED SAVAJINKS

[75] Inventor: F. Harmon Saville, Rowley, Mass.

[73] Assignee: Nor'East Miniagure Roses, Inc., Rowley, Mass.

[21] Appl. No.: 940,630

[22] Filed: Sep. 4, 1992

[51] Int. Cl.[5] ..... A01H 5/00

[52] U.S. Cl. ..... Plt./7.1

[58] Field of Search ..... Plt./7.1, 9, 10

*Primary Examiner*—Howard J. Locker
*Assistant Examiner*—E. F. McElwain
*Attorney, Agent, or Firm*—Christie, Parker & Hale

[57] ABSTRACT

A new miniature rose with red and white bicolor flowers of good form.

1 Drawing Sheet

SUMMARY OF THE INVENTION

The present invention relates to a new and distinct variety of rose plant of the miniature rose class, which was created by me by crossing as seed parent the variety known as 'Rise 'N Shine' (U.S. Plant Pat. No. 4,231) and as pollen parent the variety known as 'Sheri Anne' (U.S. Plant Pat. No. 3,826). The varietal denomination of this new rose is 'Savajinks'.

Among the novel characteristics possessed by this new variety which distinguishes it from its parent and all other varieties of which I am aware is its unusual pink and white bicolor flowers of good form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart.

Parentage:

*Seed parent.*—'Rise 'N Shine'.

*Pollen parent.*—'Sheri Anne'.

Class: Miniature.

The following observations are made of specimens grown outdoor in Essex County, Mass., during the month of July.

FLOWER

Blooming habit: Recurrent, continuous.

A. Bud:

(1) *Size.*—Medium.

(2) *Form.*—Ovoid, pointed.

(3) *Color.*—As sepals divide, bud color is near 53D washing into near white toward petal base.

(4) *Sepals.*—Smooth some with slight foliation.

(5) *Peduncle.*—Length — about 1 inch. Aspect — straight. Strength — erect. Color — near 144B.

B. Bloom:

(1) *Size.*—Average size when fully expanded — about 1⅝ inches in diameter.

(2) *Borne.*—Singly and several together in large sprays.

(3) *Form.*—Outer petals reflex and quill to points, inner petals quill and roll under.

(4) *Petalage.*—Number of petals under normal conditions — about 27 to 32.

(5) *Color.*—After sepals divide petal undersurface appears as magenta (red-purple) with near white toward petal base extending and washing into magenta coloration without defined boundary. At about ⅓ to ½ open stage, petal top surface of outer petals are near 63D to 54A at petal margin washing into pinkish-white color of balance of petals with overall coloration of near 62A–62D extending from deeper toned margins. Inner petals have less white coloring and are closer to 63B to 67A but with white highlights. Petal veination, where conspicuous, tends to be deeper colored than areas between veins. Reverse of petals in near 53D flushed with very pale yellow, near 11D, toward point of petal attachment which is near 13C. As flowers age, reds and red-purple coloring tends to become pinker and may whiten to near white flushed with near 54B.

C. Petals:

(1) *Texture.*—Thick.

(2) *Appearance.*—Inside velvety and outside satiny.

(3) *Form.*—Fan shaped, slight point at apex.

(4) *Arrangement.*—Imbricated-regularly arranged, shingle-like.

(5) *Petaloids in Center.*—Few.

(6) *Persistence.*—Drop off cleanly.

(7) *Fragrance.*—Moderate.

(8) *Lasting quality.*—Long as a cut flower.

REPRODUCTIVE ORGANS

A. Stamens, filaments and anthers:

*Arrangement and color.*—Regularly arranged around styles. Color — near 28C.

B. Pollen:

*Color.*—near 28C.

C. Styles: Medium length.

D. Stigmas:

*Color.*—near 5D.

E. Hips:

*Shape.*—Globular.

*Size.*—about ¾ inch.

*Color.*—Orange.

*Seeds.*—Occasionally protrude.

PLANT

A. Form: Upright, compact.

B. Growth: Very vigorous.

*Height attained.*—about 24 inches.

C. Foliage: Compound 5 to 7 leaflets.

(1) *Size.*—Medium.

(2) *Quantity.*—Abundant.

(3) *Color.*—New foliage: Upper side — Near 147A. Underside — Near 147C. Old foliage: Upper side — Near 147A. Underside — Near 147C.

(4) *Shape.*—Oval, pointed.

(5) *Texture.*—upper side is semi-glossy; underside is matte.

(6) *Edge.*—Serrated.

(7) *Serration.*—Uniform, relatively shallow.

(8) *Leaf stem.*—Color — Near 148A. Under side — 146B.

(9) *Stipules.*—Medium length, slightly bearded.

(10) *Resistance to Disease.*—Blackspot — Average. Mildew — Average. Rust — Average.

D. Wood:

(1) *New wood.*—Color — Near 144A. Bark — Smooth.

(2) *Old wood.*—Color — Near 143C. Bark — Smooth.

E. Thorns:

*Quantity (main stalk).*—Ordinary.

*On laterals from stalk.*—Few.

*Form.*—Slight downward curve.

*Length.*—Medium.

*Color.*—Near 173A.

*Position.*—Irregular.

(2) *Prickles.*—None.

F. Winter Hardiness: Needs protection in servere climates.

I claim:

1. A new and distinct variety of rose plant of the miniature rose class, substantially as shown and described.

* * * * *

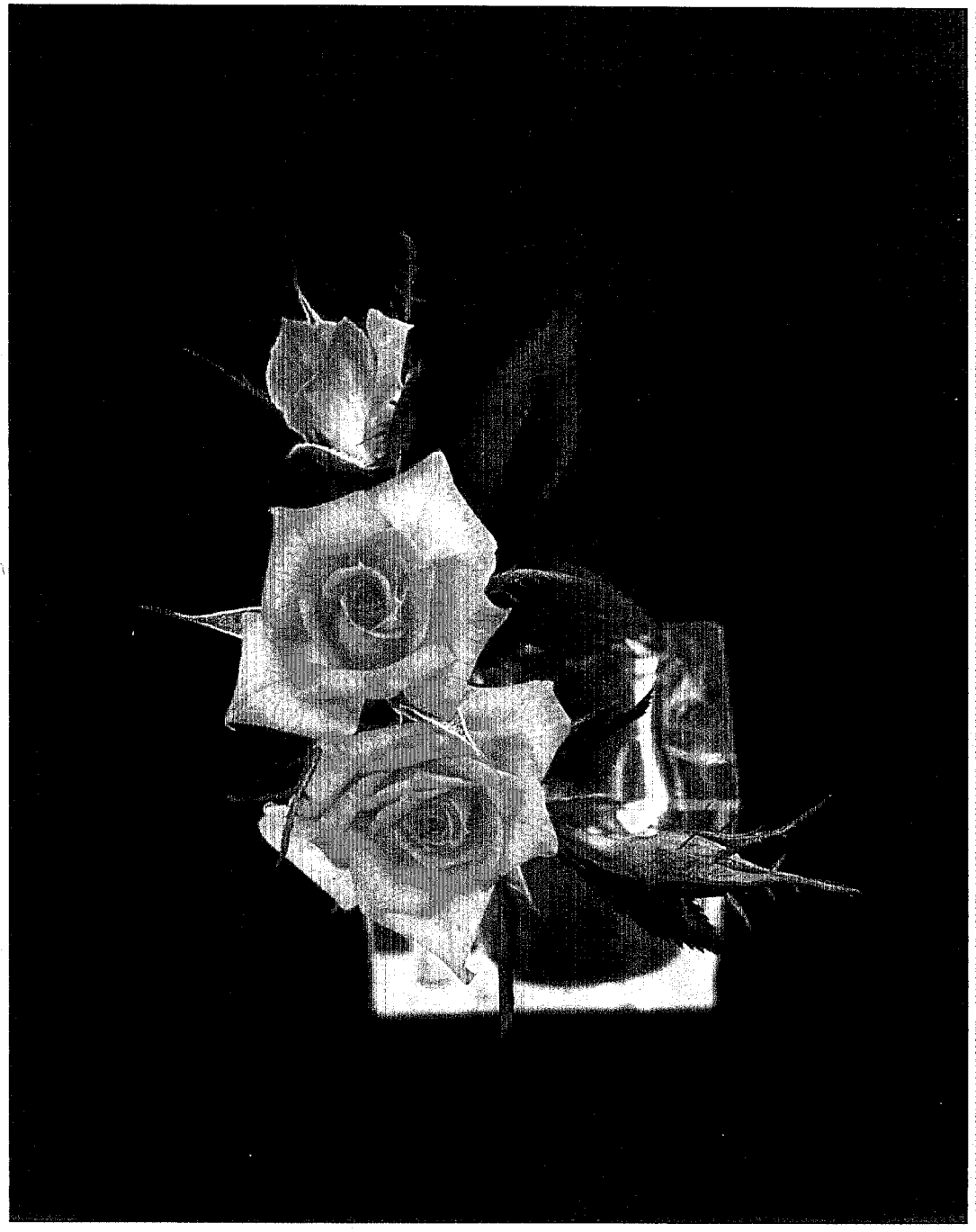

UNITED STATES PATENT AND TRADEMARK OFFICE

CERTIFICATE OF CORRECTION

PATENT NO. : Plant 8,412

DATED : October 12, 1993

INVENTOR(S) : F. Harmon Saville

It is certified that error appears in the above-indentified patent and that said Letters Patent is hereby corrected as shown below:

Column 3, line 1, change "28C" to -- 28B --.

Column 4, line 19, change "servere" to -- severe --.

Signed and Sealed this

Twenty-first Day of June, 1994

*Attest:*

Bruce Lehman

BRUCE LEHMAN

*Attesting Officer*

*Commissioner of Patents and Trademarks*